United States Patent
Shi et al.

(10) Patent No.: US 11,759,759 B2
(45) Date of Patent: Sep. 19, 2023

(54) PROCESS FOR PREPARING MICROCAPSULES WITH IMPROVED DEPOSITION

(71) Applicant: FIRMENICH SA, Satigny (CH)

(72) Inventors: Lei Shi, Shanghai (CN); Lahoussine Ouali, Satigny (CH); Lei Han, Shanghai (CN)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/979,937

(22) PCT Filed: Mar. 25, 2019

(86) PCT No.: PCT/EP2019/057459
§ 371 (c)(1),
(2) Date: Sep. 11, 2020

(87) PCT Pub. No.: WO2019/185553
PCT Pub. Date: Oct. 3, 2019

(65) Prior Publication Data
US 2021/0008518 A1    Jan. 14, 2021

(30) Foreign Application Priority Data

Mar. 30, 2018 (WO) ................. PCT/CN2018/081252
Aug. 6, 2018 (EP) ..................................... 18187425

(51) Int. Cl.
| | | |
|---|---|---|
| *B01J 13/16* | (2006.01) | |
| *A23L 27/00* | (2016.01) | |
| *A61K 8/06* | (2006.01) | |
| *A61K 8/11* | (2006.01) | |
| *C11D 3/37* | (2006.01) | |
| *C11D 3/50* | (2006.01) | |
| *C11D 17/00* | (2006.01) | |

(52) U.S. Cl.
CPC ............... *B01J 13/16* (2013.01); *A23L 27/72* (2016.08); *A61K 8/062* (2013.01); *A61K 8/11* (2013.01); *C11D 3/3773* (2013.01); *C11D 3/505* (2013.01); *C11D 17/0039* (2013.01); *A61K 2800/10* (2013.01); *A61K 2800/412* (2013.01); *A61K 2800/5426* (2013.01); *A61K 2800/56* (2013.01); *A61K 2800/594* (2013.01)

(58) Field of Classification Search
CPC ......... B01J 13/14; B01J 13/16; C11D 3/3723; C11D 3/3776; C11D 3/3773; C11D 3/505; C11D 3/3719; C11D 3/3753; C11D 17/0039; A61K 8/11; A61K 8/062; A61K 2800/412; A61K 2800/56; A61K 2800/594; A61K 2800/10; A61K 2800/5426; A23L 27/72
See application file for complete search history.

(56) References Cited

U.S. PATENT DOCUMENTS

| | | | |
|---|---|---|---|
| 8,426,353 B2 | 4/2013 | Ouali et al. | |
| 2011/0077188 A1* | 3/2011 | Ouali ...................... | B01J 13/16 512/2 |
| 2012/0148644 A1* | 6/2012 | Popplewell .............. | A61K 8/84 424/401 |
| 2013/0295149 A1* | 11/2013 | Ouali ....................... | C11B 9/00 424/401 |
| 2017/0043312 A1* | 2/2017 | Burakowska-Meise .................... | B01J 13/16 |
| 2018/0085291 A1 | 3/2018 | Sasaki et al. | |

FOREIGN PATENT DOCUMENTS

| | | | | |
|---|---|---|---|---|
| JP | 2011524805 A | 9/2011 | | |
| JP | 2017515661 A | 6/2017 | | |
| WO | 2015189309 A1 | 12/2015 | | |
| WO | WO-2016071151 A | * 5/2016 | ............. | C11D 3/505 |
| WO | 2016193435 A1 | 12/2016 | | |

OTHER PUBLICATIONS

International Search Report and Written Opinion for corresponding PCT/EP2019/057459 dated Apr. 24, 2019, 9 pages.

* cited by examiner

*Primary Examiner* — Doan T Phan
(74) *Attorney, Agent, or Firm* — Armstrong Teasdale LLP

(57) ABSTRACT

Described herein is a process for producing perfume- or flavor-containing microcapsules with improved deposition of encapsulated actives on targeted surfaces such as fiber, hair and skin, which can be used in home or personal care products. Also described herein are microcapsules obtainable by such a process and consumer products including these microcapsules.

10 Claims, No Drawings

PROCESS FOR PREPARING MICROCAPSULES WITH IMPROVED DEPOSITION

CROSS-REFERENCE TO RELATED APPLICATIONS

This application is a U.S. National Phase Application of PCT/EP2019/057459, filed Mar. 25, 2019, which claims the benefit of priority to International Patent Application No. PCT/CN2018/081252, filed Mar. 30, 2018, and which claims the benefit of priority to European Patent Application No. 18187425.6, filed Aug. 6, 2018, the entire contents of which are hereby incorporated by reference herein.

TECHNICAL FIELD

The invention relates to the field of delivery systems. More particularly, the present invention relates to a process for producing perfume- or flavor-containing microcapsules with improved deposition of encapsulated actives on targeted surfaces such as fiber, hair and skin, which can be used in home or personal care products, as well as to microcapsules obtainable by such a process and consumer products comprising these microcapsules.

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner. Polyurea capsules, formed by polymerisation between a polyisocyanate and a polyamine, are well known capsules that are used in a large variety of technical fields, including perfumery.

However such delivery systems may suffer from a poor deposition on the substrate for the treatment of which they are intended to be used, such as textile, skin, hair or other surfaces, in particular in rinse off applications wherein the capsules could be washed off leading to weak sensory perception and poor lastingness. Improving the adherence of capsules onto a surface during application is therefore desirable.

A variety of strategies have been described to improve the deposition of microcapsules on various surfaces. One of the most common solutions disclosed is based on the addition of a deposition aid or on the control of the charge of the shell of the capsules. WO2012107323 discloses for example polyurea microcapsules providing improved deposition of perfume on treated surface and which are formed by the reaction between a polyisocyanate with an amino acid and guanazole. WO2009153695 relates to a process using a specific stabilizer in the form of aqueous polymers in specific proportion to form polyurea microcapsules bearing permanent positive charges in a single step. US20060216509 also addresses that same technical problem by disclosing a process for the cationization of polyurea capsules by acidification or alkylation to bear permanent positive charges. Despite those disclosures, there is still a need to improve the deposition of the delivery systems.

SUMMARY

The process to prepare microcapsules developed in this invention is well designed to obtain microcapsules having good deposition properties. Unexpectedly, the use of at least one ionic polyvinyl alcohol with at least one cationic polymer before the emulsification step provides improvement of the deposition of said microcapsules on target surfaces such as fiber, hair and skin.

A first object of the invention is therefore a process for the preparation of a microcapsule slurry comprising the steps of:
  a) dissolving at least one polyisocyanate having at least two isocyanate groups in a hydrophobic active ingredient, preferably a perfume or flavor, to form an oil phase;
  b) dispersing the oil phase obtained in step a) into an aqueous solution comprising a mixture of at least one ionic polyvinyl alcohol with at least one cationic polymer to form an oil-in-water emulsion;
  c) applying conditions sufficient to induce interfacial polymerization to form a microcapsule slurry,
  wherein no polymeric cross-linker bearing amino groups with a molecular weight equal or higher than 2 000 g/mol is added at any stage of the process.

A second object of the present application consists of a microcapsule slurry obtainable by the above-mentioned process.

A third object of the present invention is a perfuming composition comprising
  a) microcapsules as defined above, wherein the hydrophobic active ingredient comprises a perfume;
  b) at least one ingredient selected from the group consisting of a perfumery carrier, a perfuming co-ingredient and mixtures thereof;
  c) optionally at least one perfumery adjuvant.

Another object of the present invention is a perfuming consumer product comprising the microcapsules obtained by process described above.

A last object of the invention is the use of microcapsules as defined above to prolong the release of a fragrance over time.

DETAIL DESCRIPTION OF THE INVENTION

Unless otherwise specified, percentages are meant to designate percentages by weight of a composition.

In the process of the invention, the combination of a specific emulsifier together with at least one cationic polymer allows obtaining capsules which deposit particularly well on targeted surfaces.

More particularly, the present invention advantageously solves the above-mentioned problems by forming an emulsion using a mixture of at least one ionic polyvinyl alcohol and at least one cationic polymer.

Process for Preparing a Core-Shell Microcapsule Slurry

Therefore, a first object of the present invention is a process for the preparation of a microcapsule slurry comprising the steps of:
  a) dissolving at least one polyisocyanate having at least two isocyanate groups in a hydrophobic active ingredient, preferably a perfume or flavor, to form an oil phase;
  b) dispersing the oil phase obtained in step a) into an aqueous solution comprising a mixture of at least one ionic polyvinyl alcohol with at least one cationic polymer to form an oil-in-water emulsion;
  c) applying conditions sufficient to induce interfacial polymerization to form a microcapsule slurry,
  wherein no polymeric cross-linker bearing amino groups with a molecular weight equal or higher than 2 000 g/mol is added at any stage of the process.

In a first step of the process according to the invention, at least one polyisocyanate having at least two isocyanate groups is dissolved in an oil phase comprising a hydrophobic active ingredient, preferably comprising a perfume or flavor.

Hydrophobic active ingredient: By "hydrophobic active ingredient", it is meant any hydrophobic active ingredient—single ingredient or a mixture of ingredients—which forms a two-phase dispersion when mixed with water. The hydrophobic active ingredient is liquid at about 20° C. Hydrophobic active ingredients are preferably chosen from the group consisting of flavor, flavor ingredients, perfume, perfume ingredients, nutraceuticals, cosmetics, pest control agents, biocide actives and mixtures thereof.

By "perfume or flavor" (or also "perfume or flavor oil") it is meant a perfume or flavor that is liquid at about 20° C. and which will be in the core of the core-shell capsules. According to any one of the above embodiments said perfume or flavor oil in which the polyisocyanate is dissolved in step 1) can be a perfuming or flavoring ingredient alone or a mixture of ingredients, in the form of a perfuming or flavoring composition. As a "perfuming or flavoring ingredient" it is meant here a compound, which is used in a perfuming or flavoring preparation or composition for the primary purpose of imparting a hedonic effect or modulating the odor or taste. In other words such an ingredient, to be considered as being a perfuming or flavoring one, must be able to at least impart or modify in a positive or pleasant way the odor or taste of a composition, and not just as having an odor or taste. Said ingredient can on top of their primary purpose provides secondary benefits, including but not limited to malodour counteraction, antimicrobial effect, microbial stability, food preservation, sanitization, insect repellence or taste-masking. The nature and type of the perfuming or flavoring ingredients present in the perfume or flavor oil do not warrant a more detailed description here, which in any case would not be exhaustive, a skilled person in the art being able to select them on the basis of his general knowledge and according to the intended use or application and the desired organoleptic effect sought. In general terms, these perfuming or flavoring ingredients belong to chemical classes as varied as alcohols, aldehydes, ketones, esters, ethers, acetates, nitriles, terpenoids, nitrogenous or sulphurous heterocyclic compounds and essential oils, and said perfuming or flavoring ingredients can be of natural or synthetic origin. Many of these ingredients are listed in reference texts such as the book by S. Arctander, Perfume and Flavor Chemicals, 1969, Montclair, N.J., USA, or its more recent versions, or in other works of a similar nature, as well as in the abundant patent literature in the field of perfumery or flavor. It is also understood that said ingredients may also be compounds able to release in a controlled manner various types of perfuming or flavoring compounds, including what is referred to as "pro-perfumes or pro-flavors".

In case of a perfume, the perfuming ingredient(s) to be encapsulated may be dissolved in a solvent of current use in the perfume industry. Thus, the core of the capsule might be pure perfuming ingredients or a mixture of perfuming ingredients in an adequate hydrophobic solvent.

The solvent is preferably not an alcohol. Examples of such solvents are diethyl phthalate, isopropyl myristate, Abalyn® (rosin resins, available from Eastman), benzyl benzoate, ethyl citrate and isoparaffins. Preferably, the perfume oil comprises less than 20% and more preferably less than 10% of solvent, all these percentages being defined by weight relative to the total weight of the perfume. Most preferably, the perfume is essentially free of solvent.

According to a particular embodiment of the invention, the perfume contains less than 10% of its own weight of primary alcohols, less than 15% of its own weight of secondary alcohols and less than 20% of its own weight of tertiary alcohols. Preferably, the perfume does not contain any primary alcohols and contains less than 15% of secondary and tertiary alcohols. Such limited amounts of alcohols have the advantage of reducing the amount of isocyanate functional groups reacting with the perfume.

According to any one of the invention's embodiments, the concentration of perfume is comprised between 10% and 60% by weight, relative to the total weight of the microcapsule slurry.

According to a particular embodiment, the oil phase comprises a perfume oil and the polyisocyanate.

According to a particular embodiment, the oil phase consists essentially of the perfume oil and the polyisocyanate.

According to another embodiment, the oil phase comprises a perfume together with other active ingredient(s) with the primary purpose of delivering another benefit than the perfume and to be co-released with the perfume. Non limiting example of such active include a cosmetic, skin caring, malodor counteracting, bactericide, fungicide, pharmaceutical or agrochemical ingredient, a sanitizing agent, a diagnostic agent and/or an insect repellent or attractant.

Polyisocyanate: The at least one polyisocyanate dissolved in the hydrophobic active ingredient, preferably a perfume or flavor to form the oil phase can be any type of polyisocyanate comprising at least two isocyanate groups. Preferably it contains at least three isocyanate groups.

Low volatility polyisocyanate molecules are preferred because of their low toxicity.

Preferably, the at least one polyisocyanate is an aliphatic polyisocyanate, an aromatic polyisocyanate or a mixture thereof. When the at least one polyisocyanate is in the form of a mixture of aliphatic and aromatic polyisocyanates, the at least one aliphatic polyisocyanate and the at least one aromatic polyisocyanate are preferably used in a respective molar ratio comprised between 80:20 and 10:90, more preferably between 75:25 and 20:80, even more preferably between 60:40 and 20:80 and most preferably between 60:40 and 30:70. Such molar ratio is defined as the relative ratio of the number of moles of isocyanate groups provided by the at least one aliphatic polyisocyanate and the number of moles of the isocyanate groups provided by the at least one aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N100), among which a biuret of hexamethylene diisocyanate is even more preferred.

Examples of preferred specific mixtures of at least one aliphatic polyisocyanate and of at least one aromatic polyisocyanate are mixtures of a biuret of hexamethylene diisocyanate with a trimethylol propane-adduct of xylylene diisocyanate, mixtures of a biuret of hexamethylene diisocyanate with a polyisocyanurate of toluene diisocyanate and mixtures of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate.

Preferably the at least one polyisocyanate is used in an amount comprised between 1 and 40%, preferably between 2 and 20% by weight, relative to the total weight of oil phase.

In step b) of the process of the present invention, the oil phase is dispersed into an aqueous solution comprising a mixture of at least one ionic polyvinyl alcohol and at least one cationic polymer.

This particular selection of emulsified has shown to boost the deposition properties of the capsules prepared according to the process of the invention.

The term "emulsion" is meant to designate the fact that the oil phase obtained in step a) is dispersed in an aqueous solution. The term "emulsion" is therefore understood as emulsion or dispersion. The presence of an emulsifier in the aqueous solution allows the stabilization of the oil droplets therein. In the present invention a colloidal stabilizer could be used as emulsifier. The emulsion may be prepared by high shear mixing and adjusted to the desired droplet size. Droplet size may be checked with light scattering measurements or microscopy. This procedure does not require a more detailed description as it is well known to a skilled person in the art.

The use of an ionic polyvinyl alcohol with a cationic polymer has shown to provide capsules with significantly improved deposition substrates such as hair, skin or tissue.

Emulsifier: The ionic polyvinyl alcohol defined in the present invention refers to a polyvinyl alcohol with hydroxyl and modified with functional group(s) such as quaternary ammonium, sulfonic, carboxyl groups other than hydroxyl on its side chain.

According to an embodiment, polyvinyl alcohol is modified with a functional group consisting of quaternary ammonium, sulfonic, carboxyl groups and mixtures thereof.

According to a particular embodiment, the emulsifier is a cationic polyvinyl alcohol and/or an anionic polyvinyl alcohol.

According to a particular embodiment, the emulsifier is an anionic polyvinyl alcohol.

As non-limiting examples of commercially available anionic polyvinyl alcohol, one may cite GOHSENX™ L-3266 and CKS-50, GOHSENX™ T-330, T-330H, and T-350, KURARAY POVAL KL504, KL506, KL118, KL318, KM118, KM618, and SD 1000.

As non-limiting examples of commercially available cationic polyvinyl alcohol, one may cite GOHSENX™ K-434, KURARAY POVAL C-506, C-318, C-118, and CM-318.

According to another particular embodiment, the emulsifier comprises at least two ionic polyvinyl alcohol.

The ionic emulsifier is preferably used in an amount comprised between 0.5 and 5%, more preferably between 1 and 3% by weight based on the total weight of the aqueous solution.

Cationic polymer: According to an embodiment, the cationic polymer is chosen in the group consisting of quaternized copolymer of vinylpyrrolidone and dimethylaminoethyl methacrylate, copolymer of vinylpyrrolidone and methacrylamidopropyl trimethylammonium chloride, polydiallyldimethyl ammonium chloride, copolymer of allyl dimethyl ammonium chloride/acrylamide and copolymer of acrylamidopropyltrimonium chloride and acrylamide, cationic copolymer of vinylpyrrolidone and of a quaternized vinylimidazol, guar hydroxypropyltrimonium chloride, hydrophobically modified cationic hydroxyethylcellulose and mixtures thereof.

According to an embodiment, the aqueous solution comprises two cationic polymers.

According to a particular embodiment, the two cationic polymers are a copolymer of acrylamidopropyltrimonium chloride and acrylamide and a cationic copolymer of vinylpyrrolidone and of a quaternized vinylimidazol.

According to another particular embodiment, the two cationic polymers are a copolymer of acrylamidopropyltrimonium chloride and acrylamide and a guar hydroxypropyltrimonium chloride.

The cationic polymer or the mixture of cationic polymer is preferably used in an amount comprised between 0.1 and 3%, more preferably between 0.4 and 1.5% by weight based on the total weight of the aqueous solution.

In step c) of the process of the invention, the interfacial polymerization takes place to form a microcapsule slurry.

The capsules according to the present invention have a wall that is formed by interfacial polymerization. A skilled person in the art is well aware of various ways to induce interfacial polymerization.

According to a first embodiment, capsules according to the present invention are polyurea-based capsules. According to a particular embodiment, interfacial polymerization is induced by addition of a polyamine reactant. Preferably, the reactant is selected from the group consisting of water soluble guanidine salts and guanazole to form a polyurea wall with the polyisocyanate.

The amount of polyamine used is typically adjusted so that, for each mole of isocyanate group dissolved in the perfume or flavor in step a), there is added from 0.5 to 3 moles of amine groups in step c). Preferably, for each mole of isocyanate group dissolved in the perfume or flavor in step a), 1 to 3, more preferably 1 to 2 moles of amine groups are added in step c).

The amine is preferably chosen in the group consisting of 1,2-diaminopropane, 1,2-diaminoethane, diethylenetriamine, guanidine, water soluble guanidine salts, tris-(2-aminoethyl)amine, N,N,N',N'-tetrakis(3-aminopropyl)-1,4-butanediamine, N,N'-bis(3-aminopropyl)-ethylenediamine and 3,5-diamino-1,2,4-triazole, and mixtures thereof.

According to another embodiment, polyurea-based capsules are formed in absence of added polyamine reactant, and result only from the autopolymerization of the at least one polyisocyanate, preferably in the presence of a catalyst.

According to another embodiment, capsules according to the present invention are polyurethane-based capsules. According to this particular embodiment, interfacial polymerization is induced by addition of a polyol reactant. Preferably the reactant is selected from the group consisting of monomeric and polymeric polyols with multiple hydroxyl groups available for reaction and mixtures thereof.

According to another embodiment, capsules according to the present invention are polyurea/polyurethane based. In that case interfacial polymerization is induced by addition of a mixture of the reactant mentioned under precedent first and second embodiments. Additionally, crosslinkers with both amino groups and hydroxyl groups can be used to generate polyurea/polyurethane materials. Furthermore, polyisocyanates with both urea and urethane functionalities can be used to generate polyurea/polyurethane materials.

According to another embodiment, capsules according to the present invention are organic-inorganic hybrid capsules. According to this particular embodiment, an orthosilicate, a silane or a combination of silanes can be added from the oil phase or the water phase to form a hybridized inorganic/organic membrane or surface coating. Silanes can be suspended in the oil phase to silicify the inner membrane, or can be added post-emulsification to form a silicified shell around the burgeoning polymeric capsule membrane. Inside-out and outside-in sol gel polymerization can occur by forming and hardening 3D siloxane bonds inside or outside the polymer membrane via condensation of alkoxide in or on the emulsion droplets.

Process conditions for interfacial polymerization do not need further description here as they are well known to a skilled person in the art.

During final polymerization, temperature is typically comprised between 50 and 75° C. The specific composition of the polyurea wall is key in obtaining microcapsules that are at the fine balance between release and retention so as to achieve satisfactory release of fragrances, once the capsules are placed on textiles or hair, while showing the desired stability in the product base (e.g. counteracts efficiently the extraction of the perfume by the surfactants of the consumer product) and improved deposition.

Another object of the invention is a process for preparing a core-shell microcapsule powder, said process comprises in addition to the steps a), b) and c) as defined above a step d) consisting of drying the microcapsule slurry of step c) to obtain a core-shell microcapsule powder.

The microcapsules slurry can be dried in a generally known manner to form a microcapsules powder. Any drying method known to a skilled person in the art can be used including, but not limited to fluidized bed or spray-drying tower with co-current or counter current air streams with atomizing devices of different configuration, such as two-fluid nozzles, rotary nozzles or ultrasonic nozzles. In particular the slurry may be spray-dried preferably in the presence of a polymeric carrier material such as polyvinyl acetate, polyvinyl alcohol, dextrines, maltodextrines, glucose syrups, natural or modified starch, vegetable gums, gum acacia, pectins, xanthanes, alginates, carragenans or cellulose derivatives to provide microcapsules in a powder form. A broad range of suitable spray drying configurations is available from companies like GEA-Niro (Denmark).

The microcapsule slurry obtained by the process of any of the above-described embodiments are also an object of the present invention.

According to a preferred embodiment, the present invention provides microcapsules comprising a core comprising a perfume; i.e. the microcapsules of the present invention are perfume microcapsules.

Perfuming Composition and Consumer Products

The microcapsules of the invention can be advantageously used for the controlled release of the encapsulated perfume or flavor while improving the deposition of said microcapsules on a target surface. This is particularly advantageous in the perfumery industry in what is commonly referred to as "rinse off" applications which usually suffer from the problem of losing the encapsulated perfume during rinsing and therefore hardly provide any perfume long-lasting. It is therefore particularly appreciated to include these microcapsules as perfuming ingredients in a perfuming composition or in perfumed consumer products.

Therefore, another object of the present invention is a perfuming composition comprising:
  i) perfume microcapsules as defined above;
  ii) at least one ingredient selected from the group consisting of a perfumery carrier, a perfuming co-ingredient and mixtures thereof; and
  iii) optionally at least one perfumery adjuvant.

By "perfumery carrier" it is meant a material which is practically neutral from a perfumery point of view i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. Other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996.

By "perfuming co-ingredient", it is meant an ingredient equivalent to what has been defined above as perfume ingredient. Said ingredient can take the form of a liquid oil, but can also be present in the form of a delivery system such as a perfume precursor, microcapsules, emulsions, dispersions or powders.

By "perfumery adjuvant" what is meant here is an ingredient capable of imparting additional added benefit such as a color, a particular light resistance, chemical stability, etc. A detailed description of the nature and type of adjuvant commonly used in perfuming compositions cannot be exhaustive, but it has to be mentioned that said ingredients are well known to a person skilled in the art.

An invention's composition consisting of the invention's perfume microcapsules and at least one perfumery carrier represents a particular embodiment of the invention.

The invention's microcapsules can be advantageously used in all the fields of modern perfumery, i.e. fine or functional perfumery, to positively impart or modify the odor of a consumer product into which said invention's microcapsules are added. The microcapsules according to the invention advantageously improve the long-lastingness of the perfume in such consumer products thanks to their improved deposition on the targeted surface to which the consumer product is applied. Consequently, another object of the present invention is a perfuming consumer product comprising, as perfuming ingredient, the invention's microcapsules or a perfuming composition as defined above.

The invention's microcapsules can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an effective amount of the invention's microcapsules. For the sake of clarity, said perfuming consumer product is a non-edible product.

The nature and type of the constituents of the perfuming consumer product (functional formulation and optionally benefit agents) do not warrant a more detailed description here, which in any case would not be exhaustive, the skilled person being able to select them on the basis of his general knowledge and according to the nature and the desired effect of said product.

Non-limiting examples of suitable perfuming consumer products include a fine perfume, a cologne, an after-shave lotion, a fabric care product, such as a liquid or solid detergent, a fabric softener, a fabric refresher, an ironing water, a paper, or a bleach; a body-care product, such as a hair care product (e.g. a shampoo, a hair conditioner, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent, a pet-care product such as an animal litter, a hygiene product such as a diaper, sanitary napkin, a liner or a wipe.

According to a preferred embodiment, the perfuming consumer products are preferably hair care products (e.g. a shampoo, a hair conditioner, a coloring preparation or a hair spray), and more preferably shampoos or rinse-off conditioners.

The proportions in which the microcapsules according to the invention can be incorporated into the various aforementioned articles or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the invention's microcapsules based on the weight of the composition into which they are incorporated. Concentrations lower than these, such as in the order of 0.01% to 1% by weight, can be used when these invention's microcapsules are incorporated into perfumed articles, percentage being relative to the weight of the article.

The use of the microcapsules according to the invention to prolong the fragrance release from a surface is another object of the present invention.

The invention will now be described in further details by way of the following examples, which should not be considered as limiting the invention. In the examples, unless otherwise specified, the abbreviations have the usual meaning in the art and the temperatures are indicated in degrees centigrade (° C.).

Example 1

Preparation of Core-Shell Microcapsules
(Microcapsules According to the Invention and Comparative Microcapsules)

General Procedure A

At least one polyisocyanate (Takenate®-trademark from Mitsui Chemicals-D-110N and/or Desmodur®-trademark from Bayer-N100) was dissolved in a perfume A (see table 1). The solution was poured into an aqueous solution of an emulsifier (Mowiol 18-88, Ambergum or Gum Arabic for comparative capsules and KL506, Gohsenx L-3266 or Gohsenx K-434 for capsules of the invention) and a cationic polymer, and emulsified for 3 min using an Ultra-Turrax T25 disperser at 24000 rpm to form an Oil-in-Water (O/W) emulsion. This emulsion was stirred at 400 rpm using a mechanical overhead stirrer and optionally, a NaOH aqueous solution (50 weight % in water) was added to adjust the pH. Then, a solution of polyamine e.g. guanidine carbonate was slowly added during 1 h. Once the addition of guanidine carbonate was finished, the reaction temperature was gradually elevated to between 50 and 75° C. during 1 h and was kept at 70° C. for 3 h. Finally, the formed capsule slurry was cooled down to room temperature.

TABLE 1

| Composition of perfume A | |
|---|---|
| Ingredient | wt % |
| Allyl(cyclohexyloxy)-acetate[a] | 1.2 |
| 2,4-Dimethyl-3-cyclohexene-1-carbaldehyde[b] | 1.2 |
| Menthone | 1.7 |
| Hedione ®[c] | 5.8 |
| Camphor | 2.9 |
| Eucalyptol | 5.8 |
| Dihydromyrcenol[d] | 11.5 |
| Rose oxide | 0.9 |
| Isobornyl acetate | 11.5 |
| Delta damascone | 0.6 |
| Cashmeran ®[e] | 2.3 |
| Terpenyl acetate | 5.8 |
| Lilial ®[f] | 17 |
| Linalyl acetate | 2.3 |
| Neobutenone ® alpha[g] | 1.2 |
| Dihydromycenyl acetate | 2.3 |
| 2-Methylundecanal | 3.5 |
| Iso E Super ®[h] | 11.5 |
| Cetalox ®i | 0.6 |
| Isoraldeine ® 70[j] | 2.3 |
| Habanolide ®[k] | 4.6 |
| Precyclemone B[l] | 3.5 |
| Total | 100.0 |

[a]Origin: Dragoco, Holzminden, Germany.
[b]Origin: Firmenich SA, Geneva, Switzerland.
[c]Methyl dihydrojasmonate, origin: Firmenich SA, Geneva, Switzerland
[d]Origin: International Flavors & Fragrances, USA.
[e]1,2,3,5,6,7-Hexahydro-1,2,3,3-pentamethyl-4h-inden-4-one, origin: International Flavors & Fragrances, USA.
[f]3-(4-Tert-butylphenyl)-2-methylpropanal, origin: Givaudan SA, Vernier, Switzerland.
[g]1-(5,5-Dimethyl-1-cyclohexen-1-yl)-4-penten-1-one, origin: Firmenich SA, Geneva, Switzerland.
[h]1-(Octahydro-2,3,8,8-tetramethyl-2-naphtalenyl)-1-ethanone, origin: International Flavors & Fragrances, USA.
iDodecahydro-3a,6,6,9a-tetramethyl-naphtho[2,1-b]furan, origin: Firmenich SA, Geneva, Switzerland.
[j]3-Methyl-4-(2,6,6-trimethyl-2-cyclohexen-1-yl)-3-buten-2-one, origin: Givaudan SA, Vernier, Switzerland.
[k]Pentadecenolide, origin: Firmenich SA, Geneva, Switzerland.
[l]1-Methyl-4-(4-methyl-3-pentenyl)cyclohex-3-ene-1-carboxaldehyde, origin: International Flavors & Fragrances, USA.

TABLE 2

Microcapsule compositions

| Capsule Ingredient | A wt % | Comparative A' wt % | B wt % | Comparative B' wt % | C wt % | Comparative C' wt % | D wt % | Comparative D' wt % |
|---|---|---|---|---|---|---|---|---|
| Perfume A[1] | 28.50 | 28.50 | 28.50 | 28.50 | 28.50 | 28.50 | 28.50 | 28.50 |
| Uvinul A Plus[2] | 1.5 | 1.5 | 1.5 | 1.5 | 1.5 | 1.5 | 1.5 | 1.5 |
| Takenate ® D-110N[3] | 5.24 | 5.24 | 5.24 | 5.24 | 5.24 | 5.24 | 5.24 | 5.24 |
| Guanidine carbonate | 0.88 | 0.88 | 0.88 | 0.88 | 0.88 | 0.88 | 0.88 | 0.88 |
| KL506[4] | 1.36 | 0 | 1.36 | 0 | 1.36 | 0 | 1.36 | 0 |
| Mowiol 18-88[4'] | 0 | 0.11 | 0 | 0.11 | 0 | 0.11 | 0 | 0.11 |
| Salcare SC60[5] | 0.70 | 0.70 | 0.00 | 0.00 | 0.00 | 0.00 | 0.00 | 0.00 |
| Luviquat Style[6] | 0.00 | 0.00 | 3.50 | 3.50 | 0.00 | 0.00 | 0.00 | 0.00 |
| Softcat SX1300X[7] | 0.00 | 0.00 | 0.00 | 0.00 | 0.70 | 0.70 | 0.00 | 0.00 |
| Jaguar C13S[8] | 0.00 | 0.00 | 0.00 | 0.00 | 0.00 | 0.00 | 0.70 | 0.70 |
| NaOH | 0.20 | 0.20 | 0.20 | 0.20 | 0.20 | 0.20 | 0.20 | 0.20 |
| Water | 61.62 | 62.87 | 58.82 | 60.07 | 61.62 | 62.87 | 61.62 | 61.62 |

[1] See table 1.
[2] Used as a tracer for the quantification of oil deposition, origin: BASF, Germany
[3] Trimethylol propane-adduct of xylylene diisocyanate, origin: Mitsui Chemicals, Inc., Japan.
[4] Modified polyvivyl alcohol with carboxylic group, origin: Kuraray Specialities Europe GmbH, Germany
[4'] Neutral polyvivyl alcohol, Origin Kuraray Specialities Europe GmbH, Mitsui Chemicals
[5] Copolymer of acrylamidopropyltrimonium chloride and acrylamide, origin: BASF, Germany.
[6] Copolymer of 55% vinylpyrrolidone and 45% quaternized vinylimidazole, supplied as a 19-21% solution in water, origin: BASF, Germany.
[7] Hydrophobically modified cationic hydroxyethylcellulose, origin: Dow Chemical, USA.
[8] Guar hydroxypropyltrimonium chloride. Origin: Solvay, Belgium

TABLE 3

Microcapsule compositions

| Ingredient | Capsule E wt % | Capsule F wt % | Capsule G wt % | Capsule H wt % | Capsule I wt % | Comp Capsule X wt % | Comp Capsule Y wt % |
|---|---|---|---|---|---|---|---|
| Perfume[1] | 28.50 | 28.50 | 28.50 | 28.50 | 28.50 | 28.50 | 28.50 |
| Uvinul A Plus[2] | 1.5 | 1.5 | 1.5 | 1.5 | 1.5 | 1.5 | 1.5 |
| Takenate ® D-110N[3] | 5.24 | 5.24 | 5.24 | 5.24 | 5.24 | 5.24 | 5.24 |
| Guanidine carbonate | 0.88 | 0.88 | 0.88 | 0.88 | 0.88 | 0.88 | 0.88 |
| KL506[5] | 1.36 | 1.36 | 0.00 | 0.00 | 0.00 | 0.00 | 0.00 |
| Gohsenx L-3266[6] | 0.00 | 0.00 | 1.00 | 1.00 | 0.00 | 0.00 | 0.00 |
| Gohsenx K-434[7] | 0.00 | 0.00 | 0.00 | 0.00 | 1.36 | 0.00 | 0.00 |
| Gum Arabic[8] | 0.00 | 0.00 | 0.00 | 0.00 | 0.00 | 1.50 | 0.00 |
| Ambergum 1221[9] | 0.00 | 0.00 | 0.00 | 0.00 | 0.00 | 0.00 | 1.20 |
| Salcare SC60[10] | 0.60 | 0.60 | 0.70 | 0.60 | 0.60 | 0.70 | 0.20 |
| Luviquat Style[11] | 3.00 | 0.00 | 0.00 | 0.00 | 0.00 | 0.00 | 0.00 |
| Softcat SX1300H[12] | 0.00 | 0.00 | 0.00 | 0.00 | 0.00 | 0.00 | 0.00 |
| Softcat SX400X[12] | 0.00 | 0.00 | 0.00 | 0.00 | 0.00 | 0.00 | 0.00 |
| Jaguar C13S[13] | 0.00 | 0.10 | 0.00 | 0.10 | 0.10 | 0.00 | 0.00 |

TABLE 3-continued

Microcapsule compositions

| Ingredient | Capsule E wt % | Capsule F wt % | Capsule G wt % | Capsule H wt % | Capsule I wt % | Comp Capsule X wt % | Comp Capsule Y wt % |
|---|---|---|---|---|---|---|---|
| NaOH | 0.20 | 0.20 | 0.20 | 0.20 | 0.20 | 0.20 | 0.20 |
| Water | 58.72 | 61.62 | 61.98 | 61.98 | 61.62 | 61.48 | 62.28 |

[1] See table 1
[2] Used as a tracer for the quantification of oil deposition, origin: BASF, Germany.
[3] Trimethylol propane-adduct of xylylene diisocyanate, origin: Mitsui Chemicals, Inc., Japan.
[4] Polyvinyl alcohol, origin: Kuraray Specialities Europe GmbH, Germany
[5] Modified polyvinyl alcohol with carboxylic group, origin: Kuraray Specialities Europe GmbH, Germany.
[6] Modified polyvinyl alcohol with sulfonic group on its side chain, origin: the Nippon Synthetic Chemical Industry Co., Ltd., Japan.
[7] Modified polyvinyl alcohol having a cationic group (quaternary ammonium salt) on its side chain., origin: the Nippon Synthetic Chemical Industry Co., Ltd., Japan.
[8] Origin: Nexira, France.
[9] Carboxymethyl cellulose, origin: Ashland Inc. USA.
[10] Copolymer of acrylamidopropyltrimonium chloride and acrylamide, origin: BASF, Germany.
[11] Copolymer of 55% vinylpyrrolidone and 45% quaternized vinylimidazole, supplied as a 19-21% solution in water, origin: BASF, Germany.
[12] Hydrophobically modified cationic hydroxyethylcellulose, origin: Dow Chemical, USA.
[13] Guar hydroxypropyltrimonium chloride. Origin: Solvay, Belgium.

The synthesis of comparative capsules X and Y failed during the emulsification step (resulting in semisolid) due to the precipitation when mixing the emulsifier with cationic polymers in an aqueous solution.

Example 2

Preparation of Comparative Core-Shell Microcapsules

Comparative microcapsules were also prepared according to the protocol explained in Example 1 "General procedure" except that the cationic polymer was not added at the same time as the ionic polyvinyl alcohol but after the curing step.

General Procedure B

At least one polyisocyanate (Takenate®-trademark from Mitsui Chemicals-D-110N and/or Desmodur®-trademark from Bayer-N100) was dissolved in a perfume. The solution was poured into an aqueous solution of KL506 (Modified polyvivyl alcohol with carboxylic group, origin: Kuraray Specialities Europe GmbH, Germany) and emulsified for 3 min using an Ultra-Turrax T25 disperser at 13500 rpm to form an Oil-in-Water (O/W) emulsion. This emulsion was stirred at 400 rpm using a mechanical overhead stirrer and optionally, a NaOH aqueous solution (50 weight % in water) was added to adjust the pH. Then, a solution of polyamine e.g. guanidine carbonate was slowly added during 1 h. Once the addition of guanidine carbonate was finished, the reaction temperature was gradually elevated to between 50 and 75° C. during 1 h and was kept at 70° C. for 3 h. Then a solution of cationic polymer(s) was added and stirred for 0.5 h. Finally, the formed capsule slurry was cooled down to room temperature.

TABLE 4

Microcapsule compositions

| Ingredient | Comp J wt % | Comp K wt % | Comp L wt % | Comp M wt % |
|---|---|---|---|---|
| Perfume A[1] | 28.50 | 28.50 | 28.50 | 28.50 |
| Uvinul A Plus[2] | 1.5 | 1.5 | 1.5 | 1.5 |
| Takenate ® D-110N[3] | 5.24 | 5.24 | 5.24 | 5.24 |
| Guanidine carbonate | 0.88 | 0.88 | 0.88 | 0.88 |
| KL506[4] | 1.36 | 1.36 | 1.36 | 1.36 |
| Salcare SC60[5] | 0.70 | 0.00 | 0.00 | 0.00 |
| Luviquat Style[6] | 0.00 | 3.50 | 0.00 | 0.00 |
| Softcat SX1300X[7] | 0.00 | 0.00 | 0.70 | 0.00 |
| Jaguar C13S[8] | 0.00 | 0.00 | 0.00 | 0.70 |
| NaOH | 0.20 | 0.20 | 0.20 | 0.20 |
| Water | 61.62 | 58.82 | 61.62 | 61.62 |

[1] See table 1.
[2] Used as a tracer for the quantification of oil deposition, origin: BASF, Germany
[3] Trimethylol propane-adduct of xylylene diisocyanate, origin: Mitsui Chemicals, Inc., Japan.
[4] Modified polyvinyl alcohol with carboxylic group, origin: Kuraray Specialities Europe GmbH, Germany
[5] Copolymer of acrylamidopropyltrimonium chloride and acrylamide, origin: BASF, Germany.
[6] Copolymer of 55% vinylpyrrolidone and 45% quaternized vinylimidazole, supplied as a 19-21% solution in water, origin: BASF, Germany.
[7] Hydrophobically modified cationic hydroxyethylcellulose, origin: Dow Chemical, USA.
[8] Guar hydroxypropyltrimonium chloride. Origin: Solvay, Belgium

Example 3

Performance of Microcapsules in a Shampoo

TABLE 5

Composition of the shampoo formulation

| Ingredient | Amount (wt %) |
|---|---|
| Jaguar C-14S[1] | 0.4% |
| Dehyton AB-30[2] | 7% |
| Texapon NSO IS[3] | 45.0% |
| Dow Corning 2-1691[4] emulsion | 3% |
| Cutina AGS[5] | 0.9% |
| Rewomid IPP 240[6] | 1.2% |
| Cetyl alcohol | 1.2% |

TABLE 5-continued

Composition of the shampoo formulation

| Ingredient | Amount (wt %) |
|---|---|
| Glydant plus liquid[7] | 0.3% |
| Water | 41% |

[1] Guar gum, 2 hydroxy-3-(trimethylammonium)propyl ether chloride, origin: Rhodia, La Defense, France
[2] Coco Betain, origin: Cognis, Monheim am Rhein, North Rhine-Westphalia, Germany
[3] Sodium lauryl ether sulfate + 2EO, origin: Cognis, Monheim am Rhein, North Rhine-Westphalia, Germany
[4] dimethyl(oxo)silane, origin: Dow Corning Corporation, Midland, USA
[5] Ethylene glycol distearate origin: Cognis, Monheim am Rhein, North Rhine-Westphalia, Germany
[6] Cocamide MIPA, origin: Degussa, Essen, Germany
[7] DMDM hydantoin and iodopropynyl butylcarbamate, origin: Lonza For the quantification of deposition, the following procedure was used. A hair swatch (500 mg) was wetted with 40 mL of tap water flowing at 36-40° C. Excess water was removed by manually squeezing once. 0.2 mL of unperfumed shampoo was applied along the length of swatch and agitated by fingers. The swatch was rinsed with 100 mL running water and excess water was removed again by squeezing. Then 0.2 mL of shampoo containing 1.33% by weight of capsules prepared according to examples 1 and 2 relative to the total weight of the shampoo (i.e. shampoo contained 0.4% perfume) was applied along the length of swatch and agitated by fingers. The swatch was then rinsed with 100 mL running water and excess water was shaken off. The treated part of the swatch was cut into a glass vial and dried at 60-75° C. Three repetitions of swatches were treated for reproducibility. 5 ml of ethanol was added to the dry hair and the vial was shaken for 1 h to extract any deposit. The extract was filtered, concentrated and measured on an HPLC for UV absorption. The efficiency of the deposition of the capsules could be determined by comparing the UV absorption of the extract from treated hair swatch versus that directly from 0.2 mL shampoo containing capsules prepared according to examples 1 and 2. The results are shown in Table 6 and 7.

TABLE 6

Deposition results

| Capsules | Deposition Efficiency[1] |
|---|---|
| A | 6.33% |
| Comparative A' | 3.6% |
| B | 4.21% |
| Comparative B' | 3.74% |
| C | 3.53% |
| Comparative C' | 1.99% |
| D | 2.23% |
| Comparative D' | 1.76% |
| Capsule E | 8.47% |
| Capsule F | 14.72% |
| Capsule G | 10.88% |
| Capsule H | 10.88% |
| Capsule I | 12.3% |

One can conclude from those results that the use of an ionic polyvinyl alcohol (anionic or cationic) instead of a neutral polyvinyl alcohol in the process for preparing microcapsules improves the deposition.

One can also note that the use of a combination of two cationic emulsifiers as defined in the present invention significantly improves the deposition.

TABLE 7

Deposition results

| Capsules | Deposition Efficiency |
|---|---|
| A | 6.33% |
| Comparative J | 0.33% |
| B | 4.21% |
| Comparative K | 0.13% |
| C | 3.53% |
| Comparative L | 0.26% |
| D | 2.23% |
| Comparative M | 0.22% |

One can conclude from those results that the use of a cationic polymer prior the emulsification step greatly improves the deposition instead of adding it after the curing step.

The invention claimed is:

1. A process for the preparation of a microcapsule slurry comprising the steps of:
   a) dissolving at least one polyisocyanate having at least two isocyanate groups in a hydrophobic active ingredient to form an oil phase;
   b) dispersing the oil phase obtained in step a) into an aqueous solution comprising a mixture of at least one ionic polyvinyl alcohol with at least two cationic polymers to form an oil-in-water emulsion, wherein the ionic polyvinyl alcohol is added in an amount comprised from 0.5 and 5% by weight, based on the total weight of the aqueous solution; and
   c) applying conditions sufficient to induce interfacial polymerization to form a microcapsule slurry;
wherein no polymeric cross-linker bearing amino groups with a molecular weight equal or higher than 2 000 g/mol is added at any stage of the process;
wherein the at least two cationic polymers are selected from the group consisting of quaternized copolymers of vinylpyrrolidone and dimethylaminoethyl methacrylate, copolymers of vinylpyrrolidone and methacrylamidopropyl trimethylammonium chloride, copolymers of allyl dimethyl acrylamide and copolymers of acrylamidopropyltrimonium chloride and acrylamide, cationic copolymers of vinylpyrrolidone and of a quaternized vinylimidazol, guar hydroxypropyltrimonium chloride, hydrophobically modified cationic hydroxyethylcellulose and mixtures thereof.

2. The process according to claim 1, characterized in that the ionic polyvinyl alcohol is an anionic polyvinyl alcohol.

3. The process according to claim 1, characterized in that a cross-linker selected from the group consisting of an amine, a polyol and a mixture thereof is added during step c).

4. The process according to claim 3, characterized in that the amine is selected from the group consisting of 1,2-diaminopropane, 1,2-diaminoethane, diethylenetriamine, guanidine, water soluble guanidine salts, tris-(2-aminoethyl) amine, N,N,N',N'-tetrakis(3-aminopropyl)-1,4-butanediamine, N,N'-bis(3-aminopropyl)-ethylenediamine and 3,5-diamino-1,2,4-triazole, and mixtures thereof.

5. The process according to claim 1, characterized in that microcapsules are polyurea microcapsules and wherein step c) is carried out in the absence of a cross-linker selected from the group consisting of an amine, a polyol and a mixture thereof.

6. The process according to claim 1, characterized in that the at least two cationic polymers are added in an amount comprised from 0.1 and 3% by weight, based on the total weight of the aqueous solution.

7. The process according to claim 1, characterized in that the at least one polyisocyanate is selected from the group consisting of a polyisocyanurate of toluene diisocyanate, a trimethylol propane-adduct of toluene diisocyanate, a trimethylol propane-adduct of xylylene diisocyanate, a trimer of hexamethylene diisocyanate, a trimer of isophorone diisocyanate, a trimethylol propane-adduct of hexamethylene diisocyanate, a biuret of hexamethylene diisocyanate and mixtures thereof.

8. The process of claim 1, wherein the hydrophobic active ingredient is a perfume or flavour.

9. The process according to claim 1, characterized in that the ionic polyvinyl alcohol is added in an amount comprised from 1 and 3% by weight, based on the total weight of the aqueous solution.

10. The process according to claim 1, characterized in that the at least two cationic polymers are added in an amount comprised from 0.4 and 1.5% by weight, based on the total weight of the aqueous solution.

\* \* \* \* \*